(12) United States Patent
Ates et al.

(10) Patent No.: US 7,381,821 B2
(45) Date of Patent: Jun. 3, 2008

(54) PIPERAZINE DERIVATIVES AND THEIR USE AS SYNTHESIS INTERMEDIATES

(75) Inventors: Célal Ates, Louvain-la-Neuve (BE); Emile Cavoy, Ham-sur-Heure (BE); Didier Bouvy, Ottignies (BE)

(73) Assignee: UCB, S.A., Belgium (BE)

( * ) Notice: Subject to any disclaimer, the term of this patent is extended or adjusted under 35 U.S.C. 154(b) by 137 days.

(21) Appl. No.: 10/548,709

(22) PCT Filed: Jan. 20, 2004

(86) PCT No.: PCT/EP2004/000399

§ 371 (c)(1),
(2), (4) Date: Sep. 8, 2005

(87) PCT Pub. No.: WO2004/065360

PCT Pub. Date: Aug. 5, 2004

(65) Prior Publication Data

US 2006/0183903 A1 Aug. 17, 2006

(30) Foreign Application Priority Data

Jan. 23, 2003 (EP) .................... 03001565

(51) Int. Cl.
*C07D 241/04* (2006.01)
(52) U.S. Cl. ...................... 544/358; 544/396
(58) Field of Classification Search ...................... None
See application file for complete search history.

(56) References Cited

FOREIGN PATENT DOCUMENTS

| EP | 0 598 123 A | 5/1994 |
|---|---|---|
| GB | 2 225 320 A | 5/1990 |
| GB | 2 225 321 A | 5/1990 |
| WO | WO 00/58295 A | 10/2000 |
| WO | WO 01/79188 | * 10/2001 |
| WO | WO 01/79188 A | 10/2001 |

OTHER PUBLICATIONS

March, J. Advanced Organic Chemistry. 1992. New York: John Wiley & Sons, pp. 250-251, table 8.1.*
Krause et al. Journal of Chromatography A, 1999, 837, 51-63.*
Woolley et al. The Journal of Physical Chemistry, 1970, 74, 22, 3908-3913.*
Eliel et al. Stereochemistry of Organic Compounds, 1994, 49-53.*
Carter-Finch et al. Journal of CHromatography A, 1999, 375-385.*
Malamas et al. Journal of Medicinal Chemistry, 2000, 43(5), 995-1010. (HCAPlus record).*
Press et al. Journal of Medicinal Chemistry, 1992, 35(24), 4509-15. (HCAPlus record).*
Opalka, C. J. et al., "A Novel Synthesis of The Enantiomers of an Antihistamine Drug By Piperazine Formation From a Primary Amine", *Synthesis*, Georg Thieme Verlang. Stuttgart, De, 1995, vol. 7, No. 7, pp. 766-768. XP000979124.

* cited by examiner

*Primary Examiner*—James O. Wilson
*Assistant Examiner*—Noble Jarrell
(74) *Attorney, Agent, or Firm*—McDonnell Boehnen; Hulbert & Berghoff LLP

(57) ABSTRACT

The present invention relates to new enantiomerically pure piperazine derivatives of formula (I) wherein Y represents hydroxy or a leaving group and n is 1, 2, 3, 4 or 5, and to their use as synthesis intermediates, especially for the preparation of pharmaceutically active compounds

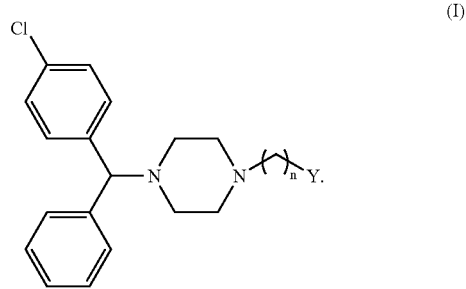

8 Claims, No Drawings

PIPERAZINE DERIVATIVES AND THEIR USE AS SYNTHESIS INTERMEDIATES

The present invention relates to new piperazine derivatives and to their use as synthesis intermediates, especially for the preparation of pharmaceutically active compounds.

Levorotatory [2-[4-[(4-chlorophenyl)phenylmethyl]-1-piperazinyl]ethoxy]acetic acid, also known by the generic name of levocetirizine, has been proven useful as therapeutic agent for the treatment of allergic diseases. Said compound may be obtained from its racemic mixture by resolution of the enantiomers of cetirizine ([2-[4-[(4-chlorophenyl)phenylmethyl]-1-piperazinyl]ethoxy]acetic acid).

GB 2,225,321 describes a process for the preparation of cetirizine in the levorotatory form, dextrorotatory form or a mixture thereof comprising the hydrolysis of enantiomerically pure or racemic [2-[4-[(4-chlorophenyl)phenylmethyl]-1-piperazinyl]ethoxy]-acetonitrile.

We have now found an alternative, more simple process for preparing enantiomerically pure compounds, such as levocetirizine, wherein a new enantiomerically pure intermediate is used.

In a first aspect, the present invention relates to enantiomerically pure compounds of formula (I), in free form or in salt form,

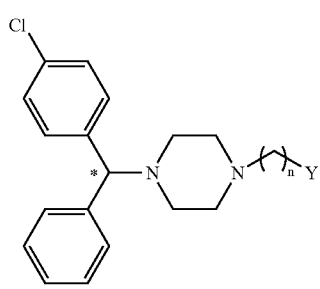

(I)

wherein

Y is hydroxy or a leaving group and n is 1, 2, 3, 4 or 5.

Compounds of formula a) include a centre of asymmetry indicated by the asterisk.

The term "enantiomerically pure compounds", as used herein, refers to compounds containing at least 90% of one enantiomer ((R) or (S)), preferably at least 98%, of the total amount of both enantiomers.

The term "leaving group", as used herein, has the same meaning to the skilled man (Advanced Organic Chemistry: reactions, mechanisms and structure—Third Edition by Jerry March, John Wiley and Sons Ed.; 1985 page 179) and represents a group which is part of and attached to a substrate molecule; in a reaction where the substrate molecule undergoes a displacement reaction (with for example a nucleophile), the leaving group is then displaced.

Preferred leaving groups are halogen, sulfonic esters such as $OSO_2—C_6H_4—CH_3$ (p-toluenesulfonate), $OSO_2—C_6H_4—Br$ (p-bromobenzenesulfonate), $OSO_2—C_6H_4—NO_2$ (p-nitrobenzenesulfonate), $OSO_2—CH_3$ (methanesulfonate), $OSO_2—CF_3$ (trifluoromethanesulfonate), $OSO_2—C_4F_9$ (nonafluorobutanesulfonate), $OSO_2—CH_2—CF_3$ (2,2,2-trifluoroethanesulfonate), $OSO_2—(CH_2)_n—NMe_3^+$ (ammoniumalkanesulfonate), $OSO_2—F$ (fluorosulfonate) and $OClO_3$ (perchlorate).

According to a preferred embodiment, n is 2.

According to another preferred embodiment, the compounds of formula a) are in the form of a (R)-enantiomer.

When in formula (I) Y represents a leaving group, it is preferably halogen, more preferably chlorine.

Compounds of formula (I) wherein Y is hydroxy or chlorine are preferred.

Compounds of formula (I) can be in free form or in salt form. In that case, dihydrochloride and dihydrobromide salts are preferred. Most preferred are dihydrochloride salts.

Compounds of formula (I) can be in the form of a solvate, which is included in the scope of the present invention. Such solvates include for example hydrates, alkoxide and the like.

Compounds of formula (I) are very stable and can be used as synthesis intermediates.

Compounds of formula (I) may be obtained by resolution of the corresponding racemic mixture which may be prepared as described in GB 2,225,320. Enantiomerically pure compounds of formula (I) can be produced using industrial chiral chromatographic separation by means of commercially available chiral stationary phases. This separation can more particularly be performed using chromatographic columns sold by DAICEL Company under the trademark CHIRALPAK AD, CHIRALPAK AS and CHIRALPAK OD. Preferred are CHIRALPAK AD columns. The process can be carried out using batch, MCC (Multi Column Chromatography) or SMB (Simulated Moving Bed) technologies.

The process is particularly efficient when mobile phases (eluents) such as alcohol, i.e. methanol, or mixtures of alcohols with alkanes are used. The preferred alkanes are hexane, isohexane and heptane. More preferred is heptane. The preferred alcohols are propanol, isopropanol, ethanol and methanol. More preferred alcohols are ethanol and methanol. The preferred mixtures are: 5% to 50% of isopropanol in hexane or in heptane, 5% to 95% of ethanol in hexane or in heptane, 1% to 10% of methanol in isohexane, and 0% to 10% of methanol, ethanol or isopropanol in acetonitrile.

Compounds of formula (I) may also be obtained by reaction of enantiomerically pure 1-[(4-chlorophenyl)phenylmethyl]piperazine, obtainable by the method described in GB 2,225,321, with a haloalkane.

In a second aspect, the present invention relates to the use of compounds of general formula (I) as synthesis intermediates, especially for the preparation of pharmaceutically active compounds.

According to a first embodiment, compounds of formula (I) are used for the synthesis of enantiomerically pure cetirizine derivatives.

Hence, a further aspect of this invention is a process for the preparation of compounds of general formula (II) as well as pharmaceutically acceptable salts thereof,

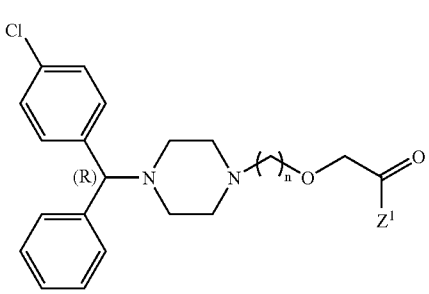

(II)

wherein

Z$^1$ represents a group of formula —OR$^1$ or —NR$^2$R$^3$, in which R$^1$ represents hydrogen, a hydrocarbon group or an alkali metal, R$^2$ and R$^3$, each independently, represent hydrogen, a hydrocarbon group or —NR$^2$R$^3$ represents a heterocycle containing up to 7 ring members, comprising the reaction of a compound of formula (I) in the form of a (R)-enantiomer and wherein Y is hydroxy, with a compound of formula (III)

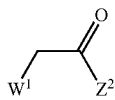

(III)

wherein W$^1$ is a halogen and Z$^2$ is as defined for Z$^1$.

The term "hydrocarbon group", as used herein, is defined as including monovalent radicals containing hydrogen and carbon atoms, such as straight, branched and cyclic alkyls, alkenyls, alkynyls, aryls, alkylaryls and arylalkyls containing 1-20 carbon atoms, preferably 1 to 4 carbon atoms for non-cyclic alkyl, 6 to 10 carbon atoms for aryl and 3 to 8 carbon atoms for cycloalkyl, as well as combinations thereof.

The term "pharmaceutically acceptable salts", as used herein, refers to salts prepared from pharmaceutically acceptable non-toxic acids or bases including inorganic acids and bases and organic acids and bases. Since the compounds of the present invention are basic, salts may be prepared from pharmaceutically acceptable non-toxic acids including inorganic and organic salts. Suitable pharmaceutically acceptable acid addition salts for the compounds of the present invention include salts of acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pantothenic, phosphoric, succinic, sulfuric, tartaric, p-toluenesulfonic acid and the like.

According to a preferred embodiment of the above mentioned process, Z$^1$ represents a group of formula —R$^1$ wherein R$^1$ is hydrogen or a C1-C4-alkyl, more preferably R$^1$ is hydrogen or methyl, most preferably R$^1$ is hydrogen.

According to another preferred embodiment of the above mentioned process, W$^1$ is chlorine.

According to another preferred embodiment of the above mentioned process, Z$^2$ represents a group of formula —OR$^1$ wherein R$^1$ is an alkali metal, more preferably R$^1$ is sodium.

The reaction of a compound of formula (I) with a compound of formula (III) is generally carried out in the presence of a chemically inert solvent and in the presence of a proton acceptor such as, for example, alkali metal hydrides, alkali metal hydroxydes, alkali metal alkoxydes or alkali metals.

Any solvent, such as aliphatic and aromatic hydrocarbons, ethers, amides and alcohols of low reactivity may be used. The preferred solvent is THF.

The reaction is generally carried out at a temperature of from 0° C. to the reflux temperature of the reaction mixture.

It was surprisingly found that no racemization occurs during that reaction.

According to a second embodiment, the compounds of formula (I) are used for the synthesis of enantiomerically pure compounds of general formula (IV). Hence, the present invention also relates to a process for the preparation of compounds of general formula (IV), as well as pharmaceutically acceptable salts thereof,

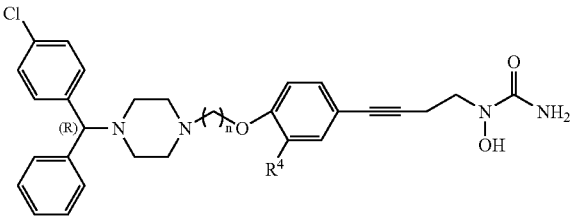

(IV)

wherein R$^4$ is hydrogen or a group of formula —C(=O)Z$^3$; Z$^3$ represents a group of formula —OR$^{1'}$ or —NR$^{2'}$R$^{3'}$, in which R$^{1'}$ represents hydrogen, a hydrocarbon group or an alkali metal, R$^{2'}$ and R$^{3'}$, each independently, represent hydrogen, a hydrocarbon group or —NR$^{2'}$R$^{3'}$ represents a heterocycle containing up to 7 ring members, comprising the use of a compound of general formula (I) in the form of a (R)-enantiomer as synthesis intermediate.

In the above mentioned process, n is preferably 2.

In the above mentioned process, R$^4$ is preferably hydrogen or —C(=O)Z$^3$ wherein Z$^3$ is —NH$_2$ or —OR$^{1'}$ wherein R$^{1'}$ is a C1-C4 alkyl, more preferably methyl. Most preferably R$^4$ is hydrogen or —CONH$_2$.

According to a first variant of this process, compounds of formula (IV) are prepared by (a) reaction of a compound of formula (V)

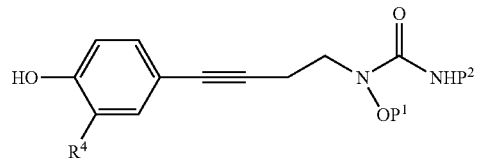

(V)

wherein P$^1$ represents a hydroxy protecting group and P$^2$ represents hydrogen or an amine protecting group, with the proviso that P$^1$ and P$^2$ may be linked to form a single protecting group when P$^2$ is not hydrogen, with a compound of formula (I) wherein Y represents a leaving group especially with a compound of formula (I) wherein Y is halogen, most preferably Cl, and (b) a deprotection step.

The term "protecting group", as used herein, refers to a substituent that is commonly employed to block or protect one or more functionalities while carrying out reactions with other functional groups on the compound. For example, an "amine protecting group" is a substituent attached to an amino group that blocks or protects the amino functionality in the compound. Suitable amine protecting groups include for example optionally substituted groups of formula —C(=O)OR or —R wherein R represents alkyl, axyl or a combination thereof. Similarly, a "hydroxy protecting group" refers to a substituent of a hydroxy group that blocks or protects the hydroxy functionality. Suitable hydroxy protecting groups include for example optionally substituted groups of formula —C(=O)OR', —R', —C(=O)R', —C(=O)NR'R" or —CR'OR", wherein R' and R" each independently represent alkyl, aryl or combinations thereof.

In case P$^1$ and P$^2$ are linked, the protecting group is preferably dialkylmethylene, more preferably isopropylene (dimethylmethylene).

Preferably, the compound of formula (V) is

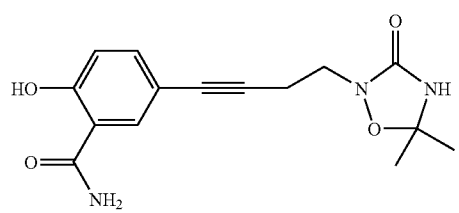
(Va)

Compounds of formula (V) may be prepared by reacting a compound of formula (VI) wherein R$^5$ is as defined for R$^4$ and W$^2$ is halogen with a compound of formula (VII), for example under Sonogashira or related conditions (ref.: Angew. Chem. Int. Ed. 2002, 41, 4176-4211).

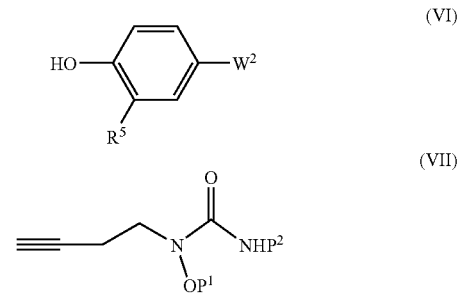

(VI)

(VII)

The reaction is generally carried out in the presence of organic or inorganic proton acceptor such as triethylamine or di-isopropylamine, and solvent such as ethylacetate, DMF, MTBE (methyl terbutyl ether), i-propylacetate, toluene, water or a mixture thereof.

Compounds of formula (VII) can for example be obtained by reacting a compound of formula (VIII) with the appropriate reagent to introduce the required protecting groups P$^1$ and p$^2$.

Compounds of formula (VIIa) are preferably obtained by reacting a compound of formula (VIII) with acetone, 2,2-dimethoxypropane or methoxypropane, in the presence of acid, preferably sulfuric acid.

The deprotection of the compound obtained from the reaction of compound (V) with compound (I) can be carried out under acidic or basic conditions depending on the nature of the protecting group.

According to a second variant of the process for the preparation of compounds of general formula (IV) this process comprises the steps of:
(a) reacting a compound of formula (I) wherein Y is a leaving group, preferably halogen, and more preferably Cl, with a compound of formula (VI) and
(b) reacting the compound thus obtained with a compound of formula (VII), preferably (VIIa), or (VIII).

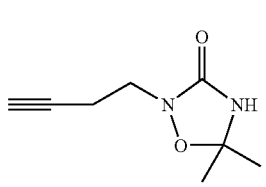
(VIIa)

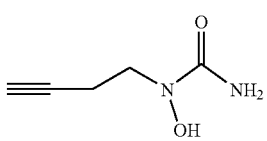
(VIII)

When a compound of formula (VII) or (VIIa) is used in this process, the process usually contains a deprotection step, such as described here above.

The reaction step (a) of a compound of formula (I) with a compound of formula (VI) generally gives rise to intermediates of formula (IX)

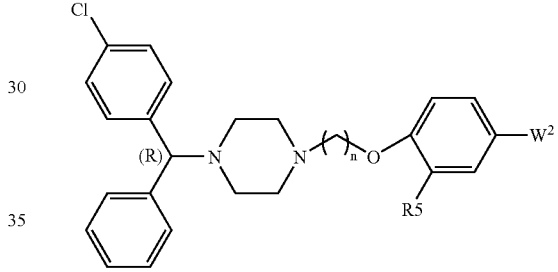
(IX)

In this variant of the process, R5 is preferably H.

International patent application WO 00/58295 describes the synthesis of compounds of formula (VIII). This patent application also describes 1,4 substituted piperazines such as compounds of formula (V) having lipoxygenase inhibition properties as well as antihistaminergic properties. However, it does not include nor suggest the use of enantiomerically pure compounds of formula (I) or the use of compounds of formula (Va), (VIIa) or (IX) as synthesis intermediates for the preparation of compounds of formula (IV).

The present invention therefore also relates to synthesis intermediates of formulae (Va), (VIIa) and (IX).

The use of compounds of general formula m as synthesis intermediates permits to produce piperazine derivatives of formula (II) and (IV) with high yield and purity, using a short and simple route. Surprisingly, no racemization of the intermediate compounds occurs under these harsh basic conditions.

The present invention will be better understood from the following examples which only serve to illustrate the invention and therefore should not be taken to limit the scope thereof. Those skilled in the art will appreciate that routine variations and modifications of the following examples can be made without exceeding the spirit or scope of the invention.

EXAMPLES

Example 1

Preparation of levocetirizine (Compound 2a, (R)-enantiomer of Compound of Formula II wherein n=2, $Z^1$=—OH)

1.1 Preparation of [2-[4-[(4-chlorophenyl)phenylmethyl]-1-piperazinyl]ethanol dihydrochloride (Racemic Mixture Compound 1a dihydrochloride)

50.1 g of sodium carbonate, 95.6 g of 1-[(4-chlorophenyl)phenylmethyl]-piperazine, 600 ml isopropanol, 45 g of 2-chloroethanol and 55 g of potassium iodide are refluxed for 24 hours. After cooling to 20-25° C., salts are filtered and rinsed with isopropanol. A isopropanol-HCl solution is dropwise added to the mechanically stirred filtrate, causing the precipitation of compound 1a dihydrochloride. The suspension is filtered and the cake is dried under vacuum at 50° C. Thus, 108 g of compound 1a dihydrochloride are obtained (Yield: 80%; Purity: >99,0%, m.p.: 158° C.).

1.2 Preparation of Compound 1a (Free Form)

265 g of sodium carbonate and then 500 g of compound 1a dihydrochloride are added to a stirred mixture of toluene (2,5l) and water (2,5l). The reaction mixture is heated to reflux. After cooling to 25° C., the toluene layer is separated and concentrated under reduced pressure to dryness to leave compound 1a free base as a liquid (385 g; Yield: 95%).

1.3 Preparation of Compound 1b (Compound of Formula I in Free Form wherein n=2, Y=OH, (R)-enantiomer)

The chromatographic separation of the enantiomers of compound 1a such as obtained in 1.2 is performed using 8 columns of 4.8×11.3 cm for 1 kg of chiral stationary phase CHIRALPAK AD (DAICEL) with methanol as the eluent.

The chromatographic parameters are:

k'1 (capacity factor of the R-enantiomer)=0.525 k'2 (capacity factor of the S-enantiomer)=1.111

Alpha (selectivity factor)=2.118

Resolution=2.164

Temperature=23° C.

Purity of (R)-enantiomer is 99.5%; ee=99%

1.4 Preparation of Compound 1b dihydrochloride 100 g of compound 1b in free form is dissolved in 500 ml of isopropanol by stirring. In another vessel, excess HCl gas is bubbled through a solution of isopropanol (500 ml). The two solutions are mixed at 20-25° C. with a mechanical agitator, which causes the precipitation of compound 1b dihydrochloride. The suspension is filtered and the cake dried under vacuum at 50° C. to yield 98 g (80% yield; >99.0% purity) of compound 1b dihydrochloride.

1.5 Preparation of Compound 2a dihydrochloride

To a stirred solution of compound 1b dihydrochloride (80 g) in THF (800 ml) at room temperature is dropwise added a mixture of potassium tert butoxide (77,8 g) in TBF (300 ml) then sodium chloroacetate (34,6 g) is added in one portion. The reaction is heated to reflux overnight, then cooled to room temperature and finally concentrated to dryness. The solid residues are dissolved in water (500 ml); the solution is acidified with concentrated HCl to pH=4,8, and then extracted twice with dichloromethane (250 ml). After evaporation of the dichloromethane, the residue is taken up in acetone (400 ml). To this solution heated at 55° C. is added a solution of HCl (10 g) in acetone (100 ml). After 30 minutes the reaction is cooled to 0° C. and maintained at 0° C. overnight. The precipitate is filtered, washed with acetone and dried under vacuum at 50° C., providing 37 g of compound 2a dihydrochloride. Purity: >96% ee

Example 2

Preparation of Compound 4a (Compound of General Formula IV wherein n=2, $R^4$=—$CONH_2$)

2.1 Preparation of Compound VIII

Reaction between commercially available 3-butyn-1-ol and methanesulfonyl chloride is performed in presence of triethylamine at 0-10° C., under vigorous stirring. As soon as the reaction is complete, hydrochloric salts of triethylamine are filtered off and washed with toluene. The collected organic phases are washed successively with aqueous $NaHCO_3$ solution, aqueous HCl solution, and finally with demineralized water. The organic phase is then evaporated under vacuum to give crude 3-butyn-1-yl methanesulfonate ester as an oil (approx. 90% yield).

Reaction between 3-butyn-1-yl methanesulfonate ester and an excess of hydroxylamine is carried out in aqueous solution in presence of methyl alcohol. When the reaction is complete, methyl alcohol is evaporated under vacuum. The solution is washed with toluene. The aqueous phase is then washed with ethyl acetate to extract N-(3-butyn-1-yl) hydroxylamine. The organic phases containing N-(3-butyn-1-yl) hydroxylamine are collected in order to be concentrated and then directly used into the next step.

EtOAc solution of N-(3-butyn-1-yl) hydroxylamine obtained from the previous step is directly used in the next step. Into the solution are added potassium cyanate previously dissolved in demineralized water. The mixture is cooled down to 0° C., and under vigorous stirring, HCl (37% aqueous solution) is slowly added. The reaction medium is then heated to 20° C. and after decantation, the two phases are separated. Sodium chloride is added to the aqueous phase under stirring to saturation and the aqueous phase is washed with EtOAc. All the EtOAc phases are collected and evaporated under vacuum to dryness to give crude N-(3-butyn-1-yl) N-hydroxyurea (compound VIII).

2.2 Preparation of Compound VIIa

Crude compound VIII is dissolved in a mixture of acetone and 2,2-dimethoxypropane. Sulfuric acid is slowly added and the reaction mixture is heated at reflux. As soon as the reaction is complete, the mixture is cooled down, potassium carbonate is added and the mixture is stirred overnight and then filtered. The filter cake is washed with acetone. The combined organic phases are evaporated under vacuum. The evaporation is stopped when condensation is no longer observed. Water and acetone are added and the medium is maintained at 40° C. for a while. The mixture is then cooled down to 0° C. and stirred at that temperature. Compound VIIa crystallizes as a white solid and is filtered. After filtration, the cake is washed with water and toluene. The solid is then dried under vacuum to give compound VIIa (58% yield, >98 area % purity by HPLC).

2.3 Preparation of Compound Vb (Compound of Formula V wherein $R^4$=—$COOCH_3$ and $P^1P^2$=isopropylene)

The reactor is flushed with $N_2$ prior to charging material. 5-iodosalicylate methyl ester, compound VIIa, $Pd(PPH_3)_2Cl_2$, CuI, EtOAc, water, triethylamine and tetra butyl ammonium bromide are vigorously stirred. The solid compound Vb is filtered, washed with water, and then dried to give a white to off-white powder (77% yield, >98% purity).

2.4 Preparation of Compound Va

Ammonolysis of compound Vb to give compound Va is carried out under pressure in methanol, isopropanol, tert-amyl alcohol or other pentyl alcohol at a temperature between 25° C. and 40° C. As soon as the reaction is complete, the excess of ammonia is removed and the reaction mixture is slightly concentrated in order to initiate the precipitation of the product. The suspension is then cooled down to 0° C. to complete the precipitation of compound Va. After filtration of crude product, the cake is washed with cooled alcohol.

In order to get a high purity material (>99.0%), compound Va is then recrystallized in isopropanol.

2.5 Preparation of Compound 1c (Compound of Formula I dihydrochloride salt or Free Base wherein n=2 and Y=Cl, (R)-enantiomer)

82 g of compound 1b prepared as described in Example 1, 11 of toluene, 45 g of thionyl chloride and 5 g of dimethyl formamide are successively added to a vessel. The mixture is stirred at reflux for 48 hours then cooled to room temperature. It is then filtered, washed with toluene and then dried under vacuum at 50° C. to give the compound 1c dihydrochloride salt (Yield>90%). 50 g of the filtered solid is stirred in a mixture of toluene and water and sodium carbonate (25 g) is added. The toluene layer is separated and evaporated to dryness, leaving compound 1c free base as a thick liquid (Purity: >99%).

2.6 Preparation of Compound 4a

A mixture of compound Va, compound 1c free base and $K_2CO_3$ are stirred in isopropanol or in pentyl alcohol at a temperature between 30° C. and 40° C. The reaction mixture is cooled down to room temperature and filtered. The filter cake is washed with isopropanol or pentyl alcohol.

The deprotection step is carried out at room temperature, in a mixture of HOAc, $H_2SO_4$ and water. As soon as the reaction is complete, the solvent is evaporated. The residual oil is dissolved in EtOAc and the solution is washed with saturated aqueous $NaHCO_3$ solution. The EtOAc layer is then washed twice with saturated NaCl aqueous solution. The solution is concentrated (half of the EtOAc is evaporated) using a hot water bath. The solution is stirred and allowed to cool to room temperature, and then cooled down to 0° C. The solid is filtered, washed with EtOAc and dried to give compound 4a as a white to off-white solid (70% yield, >99% purity). Purity: >96% ee.

2.7 Preparation of Compound 4a fumarate salt 100 g of compound 4a and 21 g of fumaric acid are dissolved in a mixture of ethyl acetate and ethanol at reflux. The solution is allowed to cool to 5° C. and stirred during 12 hours. The precipitate is filtered and dried under vacuum to give 102 g of compound 4a fumarate salt (Yield: 84%). The salt formation is also efficiently carried out in solvents such as ethanol, THF, mixtures of ethyl acetate/ethanol, THF/methanol or THF/ethanol.

Example 3

Preparation of Compound 4b (Compound of Formula IV wherein n=2 and $R^4$=H)

3.1 Preparation of Compound 9a oxalate (Compound of Formula IX wherein n=2, $R^5$=H and $W^2$=I)

To a suspension of compound 1c dihydrochloride salt (102.9 g) prepared as described in Example 2, in toluene (820 ml) and water (360 ml) is added iodophenol (59.01 g), potassium carbonate (118.0 g) and potassium iodide (4.05 g) then the mixture is heated to 95° C. for 24 hours, then cooled and transferred to a separating funnel. The aqueous layer is removed and the organic layer transferred to a 2L round bottomed flask. A solution of oxalic acid (24.15 g) in ethyl acetate (340 ml) is added affording a white precipitate. The precipitate is collected by suction filtration and washed with ethyl acetate to afford compound 9a oxalate as an off-white powder (149.56 g, quantitative yield).

3.2 Preparation of Compound 4b in Free Form

To a mixture of compound 9a oxalate (100 g) in toluene-THF (1:1, 1000 ml) and water (300 ml) is added diisopropylamine (79 ml), $PdCl_2(PPh_3)_2$ (1128 mg) and CuI (459 mg), then compound VIII such as prepared in Example 2 (26.8 g). After 24 hours at room temperature, the two layers are separated and to the organic layer is added activated charcoal (50 g) and the mixture is stirred overnight. The contents are filtered through a short pad of celite and the pad is washed with THF. The combined organic filtrates are then concentrated in vacuo at 45° C. to give an amorphous solid (quantitative yield).

3.3 Preparation of Compound 4b malate salt

Compound 4b in free form is dissolved with L-malic acid (23.7 g) in hot ethyl acetate (1L). The solution is allowed to cool to 10° C. and stirred overnight. The precipitate is filtered and then washed with EtOAc and finally dried under vacuum to give 87 g (81% yield) of an off-white powder which is pure by TLC, HPLC and $^1$H NMR. The salt formation is also efficiently carried out in common solvents such as ethanol, THF and mixtures of ethyl acetate/ethanol or THF/methanol or THF/ethanol.

The invention claimed is:

1. A process for preparation of compounds of formula (IV) or pharmaceutically acceptable salts thereof,

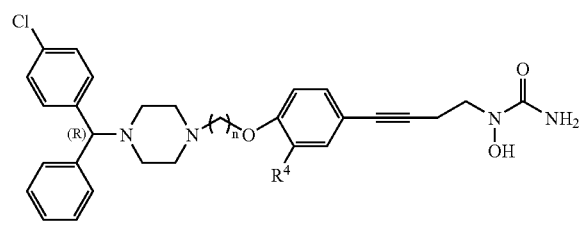

(IV)

wherein
$R^4$ represents hydrogen or a group of formula —C(=O)$Z^3$;
$Z^3$ represents a group of formula —$OR^{1'}$ or —$NR^{2'}R^{3'}$, in which $R^{1'}$ represents hydrogen, a hydrocarbon group or an alkali metal, $R^{2'}$ and $R^{3'}$, each independently, represent hydrogen or a hydrocarbon group, or —$NR^{2'}R^{3'}$ represents a heterocycle containing up to 7 ring members, and n is 1, 2, 3, 4, or 5, comprising reacting a compound of formula I:

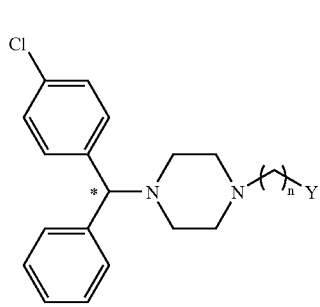
(I)

in the form of an (R)-enantiomer, wherein Y is a leaving group and n is 1, 2, 3, 4, or 5, with a compound of formula (V)

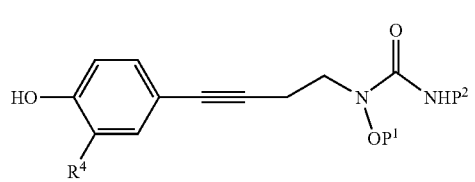
(V)

wherein $P^1$ represents a hydroxy protecting group and $P^2$ represents hydrogen or an amine protecting group, with the proviso that $P^1$ and $P^2$ are optionally linked to form a single protecting group, and deprotecting the product.

2. The process according to claim 1 wherein the compound of formula (V) is the compound of formula (Va).

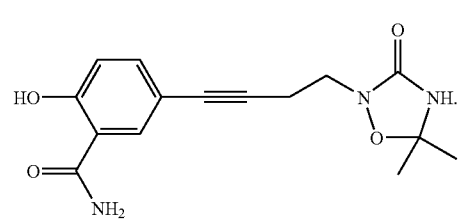
(Va)

3. The process according to claim 1 wherein the compound of formula (V) is prepared by reaction of a compound of formula (VII) with a compound of formula (VI) wherein $R^5$ is as defined for $R^4$ and $W^2$ is halogen

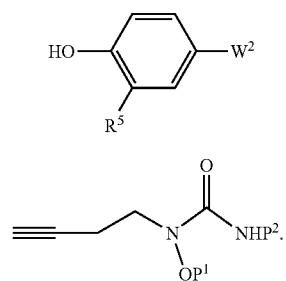
(VI)

(VII)

4. A process for preparation of compounds of formula (IV) or pharmaceutically acceptable salts thereof,

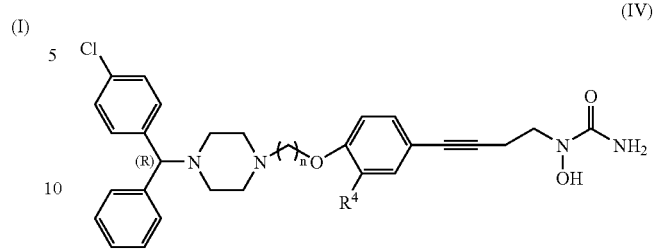
(IV)

wherein $R^4$ represents hydrogen or a group of formula —C(=O)$Z^3$; $Z^3$ represents a group of formula —OR$^{1'}$ or —NR$^{2'}$R$^{3'}$, in which R$^{1'}$ represents hydrogen, a hydrocarbon group or an alkali metal, R$^{2'}$ and R$^{3'}$, each independently, represent hydrogen or a hydrocarbon group, or —NR$^{2'}$R$^{3'}$ represents a heterocycle containing up to 7 ring members, and n is 1, 2, 3, 4, or 5 comprising reacting of a compound of formula (I)

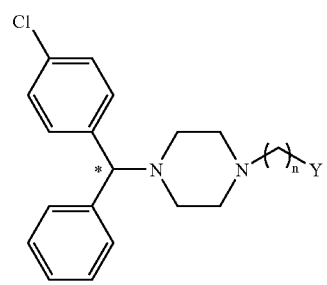
(I)

in the form of an (R)-enantiomer, wherein Y is a leaving group and n is 1, 2, 3, 4, or 5, with a compound of formula (VI)

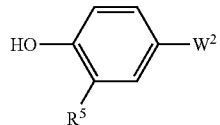

wherein $R^5$ is as defined for $R^4$ and $W^2$ is halogen, and reacting the compound thus obtained with a compound of formula (VII)

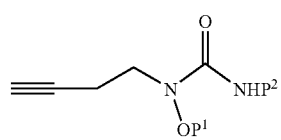

wherein $P^1$ represents a hydroxy protecting group and $P^2$ represents hydrogen or an amine protecting group, with the proviso that $P^1$ and $P^2$ are optionally linked to form a single protecting group, (VIIa) or (VIII):

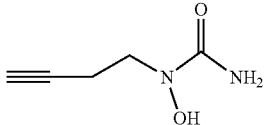
(VIII)

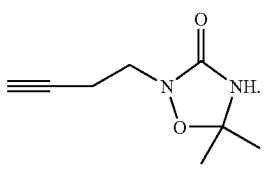
(VIIa)

5. A compound of formula (Va),

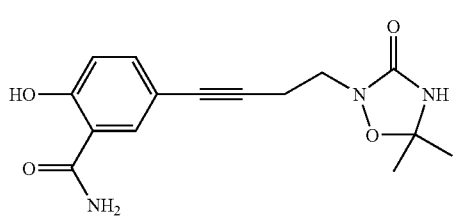
(Va)

(VIIa),

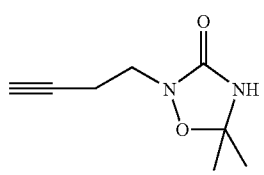
(VIIa)

or (IX)

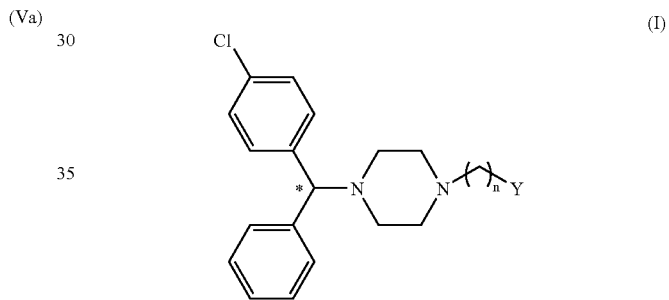
(IX)

wherein n is 1, 2, 3, 4, or 5, $R^5$ represents hydrogen or a group of formula —C(=O)$Z^3$; $Z^3$ represents a group of formula —OR$^{1\prime}$ or —NR$^{2\prime}$R$^{3\prime}$, in which R$^{1\prime}$ represents hydrogen, a hydrocarbon group or an alkali metal, R$^{2\prime}$ and R$^{3\prime}$, each independently, represent hydrogen or a hydrocarbon group, or —NR$^{2\prime}$R$^{3\prime}$ represents a heterocycle containing up to 7 ring members and $W^2$ is halogen.

6. The process of claim 1, wherein Y is Cl.

7. The process of claim 4, wherein Y is Cl.

8. An enantiomerically pure compound of formula (I) in free form or in salt form (I)

wherein

Y represents sulfonic ester or perchlorate (OClO$_3$), and n is 1, 2, 3, 4 or 5, and wherein the sulfonic ester is p-toluenesulfonate (OSO$_2$—C$_6$H$_4$—CH$_3$), p-bromobenzenesulfonate (OSO$_2$—C$_6$H$_4$—Br), p-nitrobenzenesulfonate (OSO$_2$—C$_6$H$_4$—NO$_2$), methanesulfonate (OSO$_2$—CH$_3$), trifluoromethanesulfonate (OSO$_2$—CF3), nonaflurobutanesulfonate (OSO$_2$—C$_4$F$_9$), 2,2,2-trifluoroethanesulfonate (OSO$_2$—CH$_2$—CF$_3$), and fluorosulfonate (OSO$_2$—F).

* * * * *